(12) United States Patent
Fujita

(10) Patent No.: US 8,163,239 B2
(45) Date of Patent: Apr. 24, 2012

(54) SAMPLE ANALYZER

(75) Inventor: Kyozo Fujita, Hamburg (DE)

(73) Assignee: Sysmex Corporation, Kobe (JP)

( * ) Notice: Subject to any disclaimer, the term of this patent is extended or adjusted under 35 U.S.C. 154(b) by 1072 days.

(21) Appl. No.: 11/893,792

(22) Filed: Aug. 17, 2007

(65) Prior Publication Data

US 2008/0050279 A1 Feb. 28, 2008

(30) Foreign Application Priority Data

Aug. 18, 2006 (JP) ................................. 2006-223120

(51) Int. Cl.
*G01N 21/00* (2006.01)
(52) U.S. Cl. ................ 422/64; 422/63; 422/65; 422/66; 422/67; 422/50; 422/500; 422/501; 436/180
(58) Field of Classification Search ............. 422/63–67, 422/99–100, 500–501, 50; 436/180
See application file for complete search history.

(56) References Cited

U.S. PATENT DOCUMENTS

| 4,678,752 | A | * | 7/1987 | Thorne et al. | ............... | 435/287.3 |
| 5,985,215 | A | | 11/1999 | Sakazume et al. | | |
| 2001/0028864 | A1 | * | 10/2001 | Tyberg et al. | ................. | 422/100 |

FOREIGN PATENT DOCUMENTS

| JP | 63-156072 U | 10/1988 |
| JP | 06-094729 | 4/1994 |
| JP | 10-096734 A | 4/1998 |
| JP | 10-115620 A | 5/1998 |
| JP | 2000-088862 A | 3/2000 |
| JP | 2001-264340 | 9/2001 |
| JP | 2002-162403 A | 6/2002 |

* cited by examiner

*Primary Examiner* — Jyoti Nagpaul
(74) *Attorney, Agent, or Firm* — Brinks Hofer Gilson & Lione

(57) ABSTRACT

The sample analyzer comprises a transporting device for transporting a rack for holding a plurality of containers containing samples respectively and having a recording part in which identifying information has been recorded that identifies the rack, a reading device for reading the identifying information from the recording part of the transported rack, an aspirating device including an aspirating tube for aspirating the sample from the container, a controller for controlling the operation of the aspirating device based on the identifying information read by the reading device, and an analyzing device for analyzing a measurement sample that includes the aspirated sample.

7 Claims, 16 Drawing Sheets

SAMPLE ANALYZER

RELATED APPLICATIONS

This application claims priority under 35 U.S.C. §119 to Japanese Patent Application No. 2006-223120 filed Aug. 18, 2006, the entire content of which is hereby incorporated by reference.

FIELD OF THE INVENTION

The present invention relates to a sample analyzer.

BACKGROUND

Conventional sample analyzers are known which are provided with aspirating device that includes an aspirating tube for aspirating a sample from a container that contains the sample (blood collection tube). Various types of containers which have different internal diameters, external diameters, and lengths are used as containers in such sample analyzers. Since the containers (blood collection tubes) used in individual hospitals differ, testing laboratories that analyze samples received from many hospitals must be capable of handling these various types of containers.

However, when the containers have different shapes, it becomes necessary to manage the depth to which the aspirating tube is inserted when aspirating samples from the containers since the position of the bottom of the container and the cross section area of the surface level will differ. Sample analyzers have been proposed which are configured to handle containers (blood sample collection tubes) of various shapes (for example, refer to Japanese Laid-Open Patent Publication Nos. 2001-264340 and H6-94729, and U.S. Pat. No. 5,985, 215).

In the sample analyzer disclosed in Japanese Laid-Open Patent Publication No 2001-264340, a barcode reader reads the information identifying the type of container from a barcode adhered to the container, and changes the insertion depth of the aspirating tube in accordance with the type of container.

In the sample analyzer disclosed in U.S. Pat. No. 5,985, 215, a container shape discriminating unit identifies the shape of the container, and the sample material is pipetted by a pipetting mechanism selected in accordance with the shape of the sample container. This container shape discriminating unit includes a plurality of light emitting diode arrays arranged at different heights, and an a plurality of photodiode arrays arranged at different heights. The height and width of a container are detected from the time and height the optical path is blocked by the container transported at a constant speed between the light emitting diodes and photodiodes.

The sample analyzer disclosed in Japanese Laid-Open Patent Publication No. H6-94729, has a plurality of types of containers of different heights arranged in a starting yard (initial position), and a container shape discriminating unit detects the height of the containers disposed in the starting yard. Identifying information (in a barcode) attached to the sample container is read according to the type of sample container which is recognized by height, and the respective sample containers are allocated to a plurality of sample analyzers. This container shape discriminating unit identifies the type of container by the height at which the container gripped by a transporting robot that holds the container at the starting yard.

However, in the sample analyzer disclosed in Japanese Laid-Open Patent Publication No. 2001-264340, since the information identifying the type of container is not normally included in the barcode adhered to the container at each of the hospitals that collect samples, a barcode that includes information identifying the type of container must be adhered at the testing laboratory. This replacing and re-adhering of the barcode therefore reduces testing efficiency.

In the sample analyzer disclosed in U.S. Pat. No. 5,985, 215, the structure of the analyzer is complicated due to the provision of the container shape discriminating unit that includes a plurality of light emitting diode arrays arranged at different heights, and an a plurality of photodiode arrays arranged at different heights.

In the sample analyzer disclosed in Japanese Laid-Open Patent Publication No. H6-94729, the structure of the analyzer is complicated due to the provision of a container shape discriminating unit configured to detect the type of container by the height at which a transporting robot grips the container disposed in the starting yard.

BRIEF SUMMARY

The scope of the present invention is defined solely by the appended claims, and is not affected to any degree by the statements within this summary.

The first aspect of the present invention relates to a sample analyzer comprising a transporting device for transporting a rack for holding a plurality of containers containing samples respectively, the rack comprising a recording part in which identifying information for identifying the rack is recorded, a reading device for reading the identifying information from the recording part of the rack transported by the transporting device, an aspirating device comprising an aspirating tube for aspirating the sample from the container, a controller for controlling the operation of the aspirating device based on the identifying information read by the reading device, and an analyzing part for analyzing the sample aspirated by the aspirating device.

The second aspect of the present invention relates to a sample analyzer comprising a communication device for receiving identifying information for identifying a rack for holding a plurality of containers containing samples respectively, an aspirating device comprising an aspirating tube for aspirating the sample from the container, a controller for controlling operation of the aspirating device based on the identifying information received by the communication device, and an analyzing part for analyzing the sample aspirated by the aspirating device.

The third aspect of the present invention relates to a sample analyzer comprising a transporting device for transporting a rack for holding a plurality of containers containing samples respectively, the rack comprising a recording part in which identifying information for identifying the containers held by the rack is recorded, a reading device for reading the identifying information from the recording part of the rack transported by the transporting device, an aspirating device comprising an aspirating tube for aspirating the sample from the container, a controller for controlling the operation of the aspirating device based on the identifying information read by the reading device, and an analyzing part for analyzing the sample aspirated by the aspirating device.

DETAILED DESCRIPTION OF THE PREFERRED EMBODIMENTS

The embodiments of the present invention are described hereinafter based on the drawings.

Figure 1:
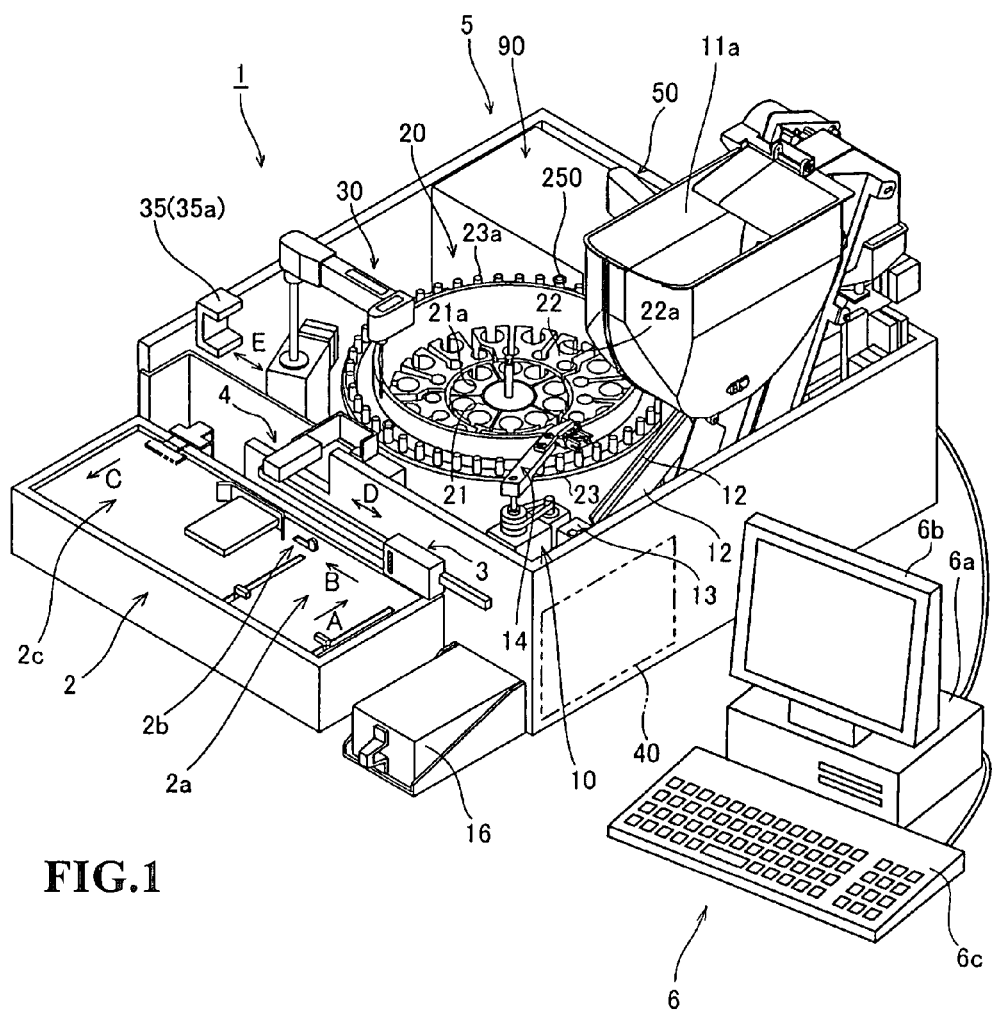
FIG. 1 is a perspective view of the general structure of an embodiment of the sample analyzer of the present invention.
Figure 2:
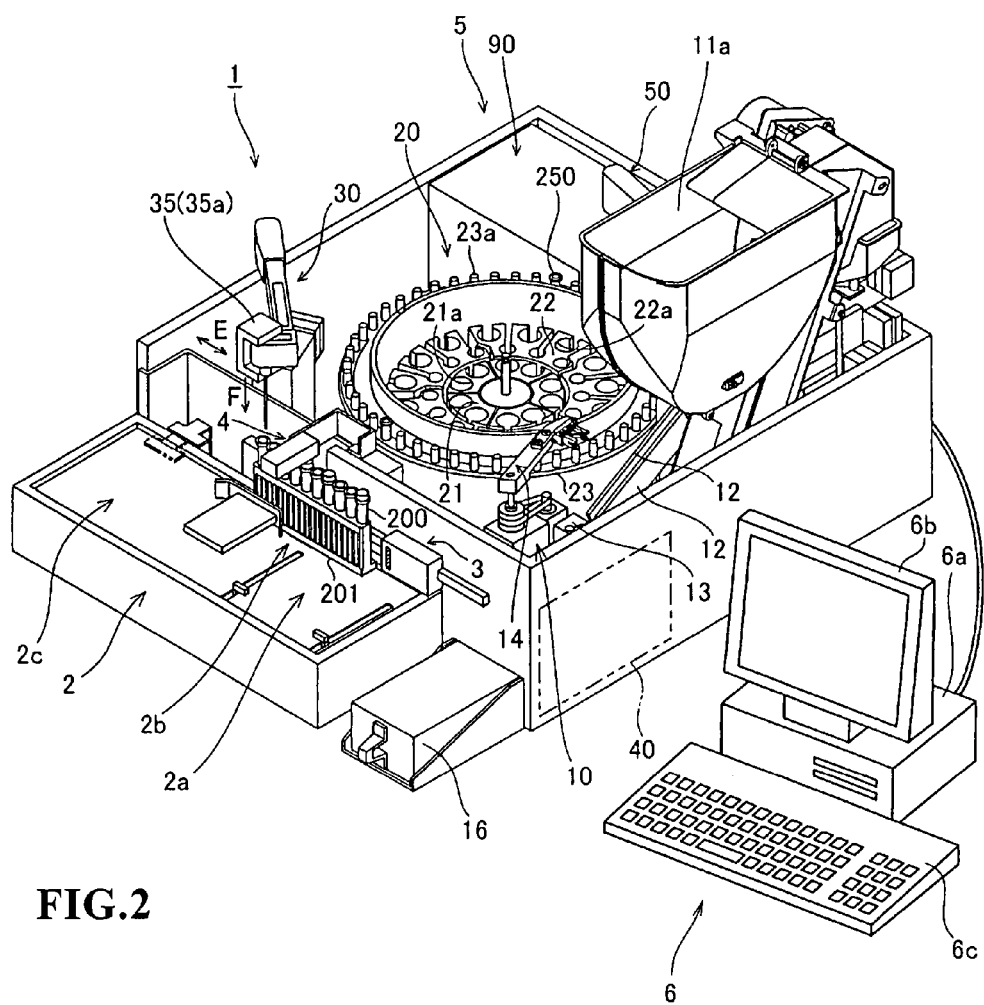
FIG. 2 is a perspective view of the general structure of an embodiment of the sample analyzer of the present invention.
Figure 3:
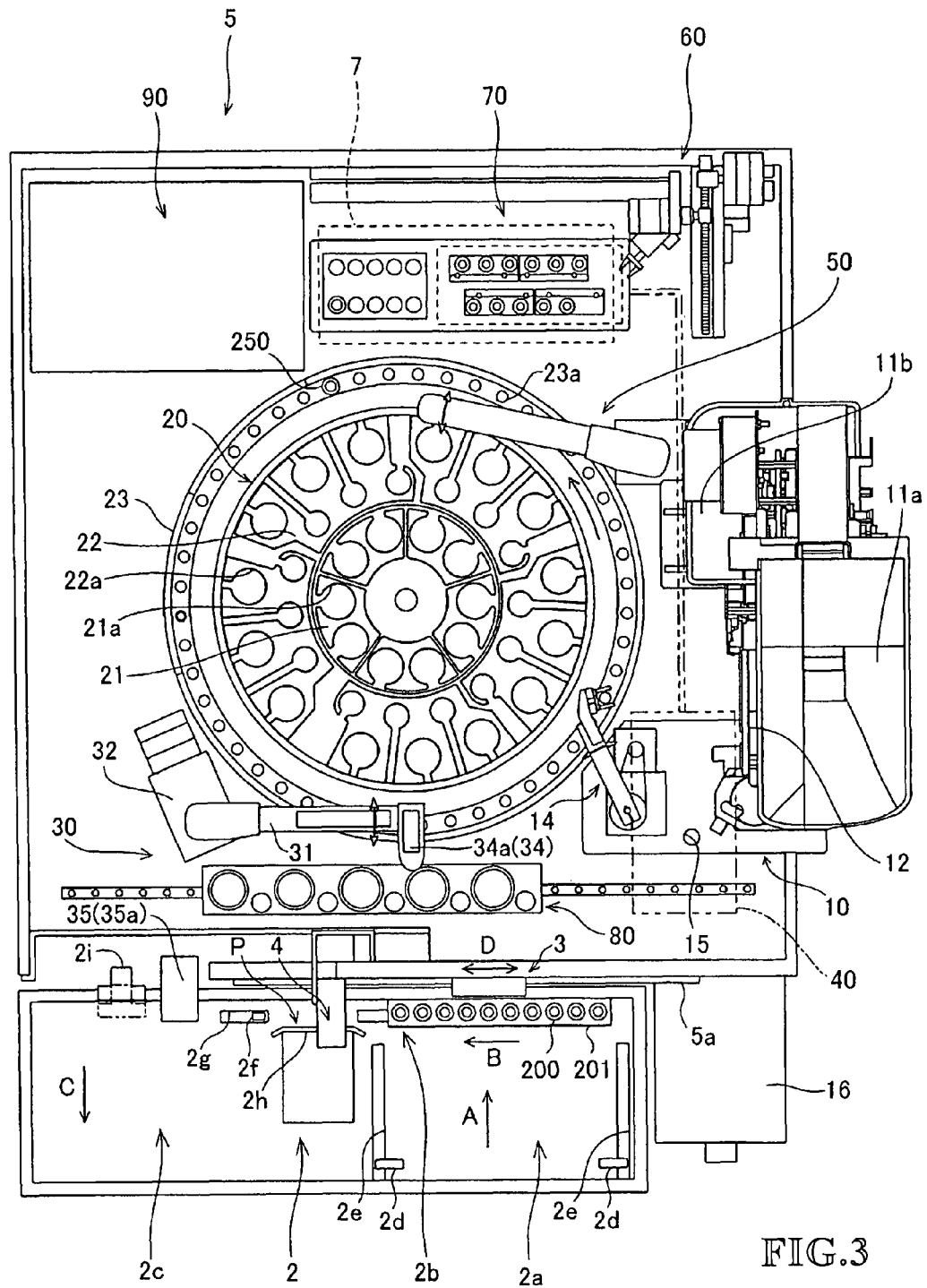
FIG. 3 is a top view of the general structure of an embodiment of the sample analyzer of FIG. 1.
Figure 4:
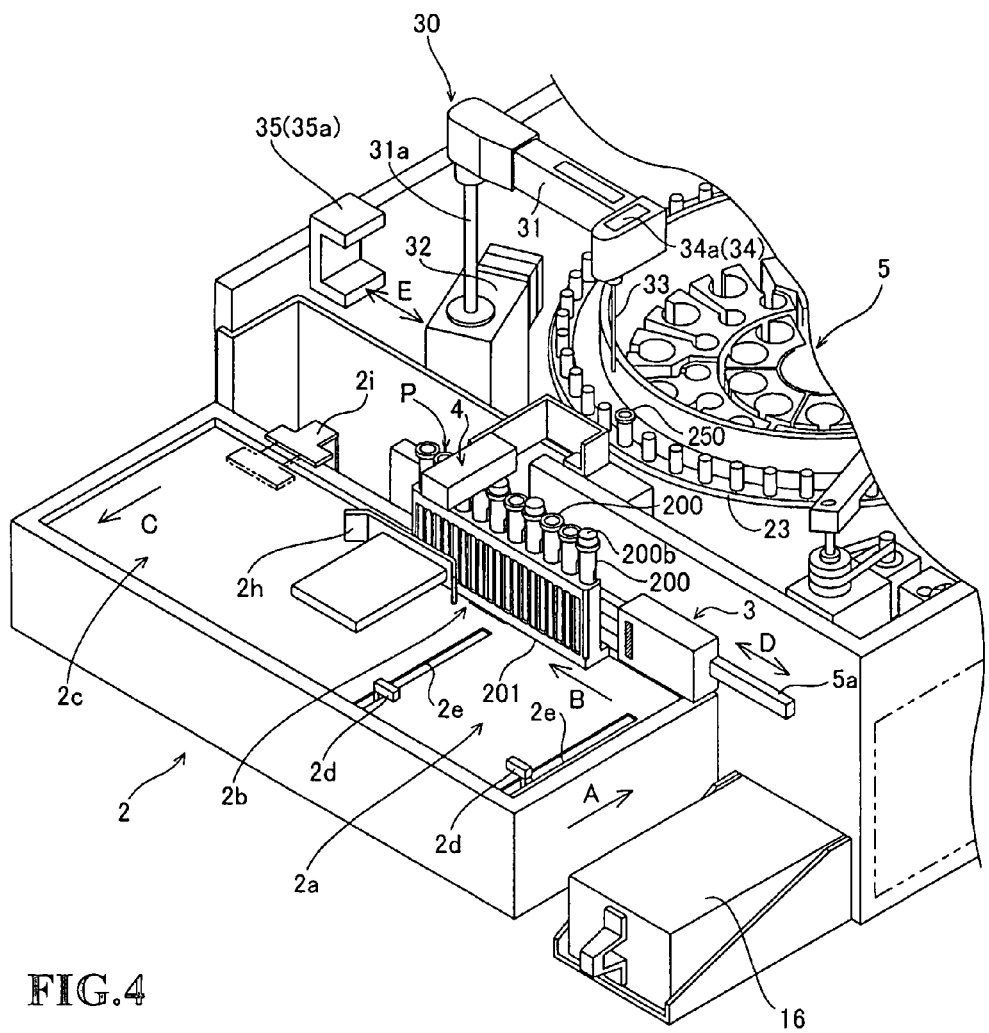
FIG. 4 is an enlarged perspective view of the transporting device, sensor, and barcode reader of the embodiment of the sample analyzer of FIG. 1.
Figure 5:
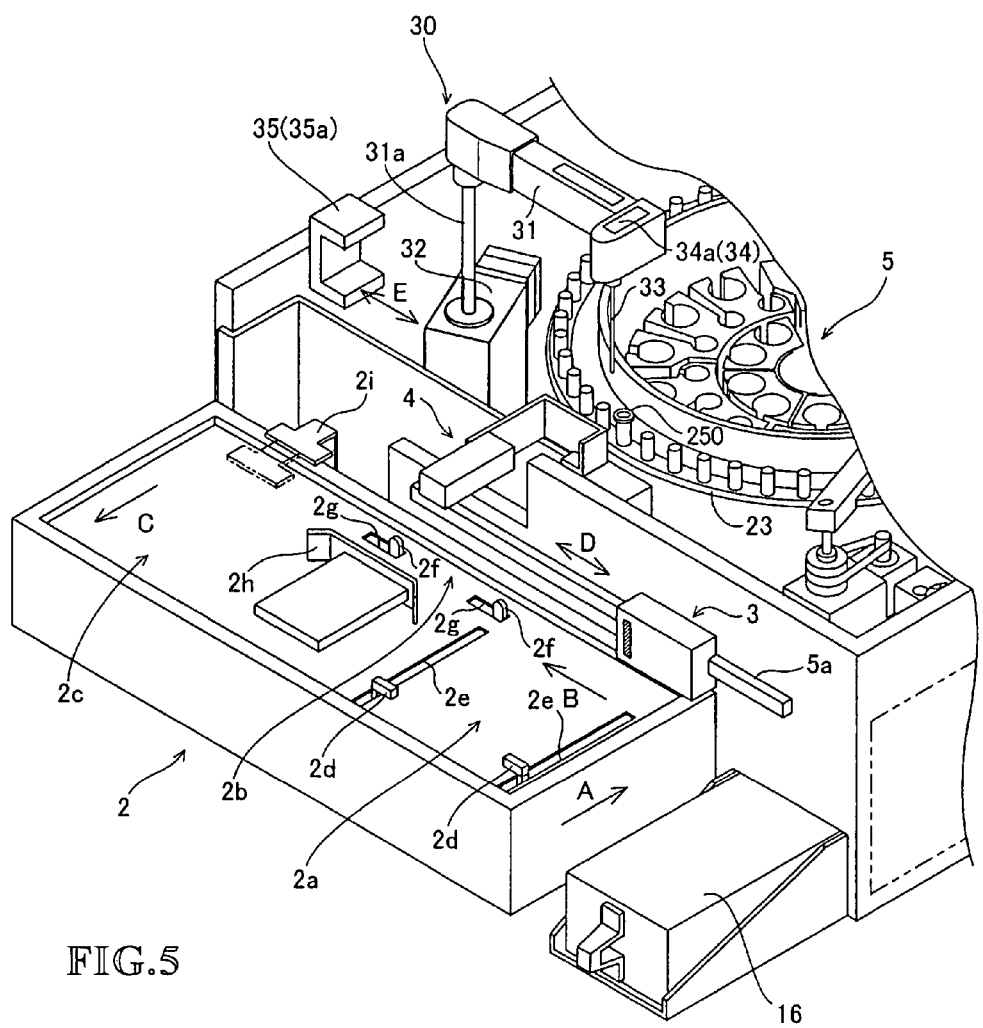
FIG. 5 is an enlarged perspective view of the transporting device, sensor, and barcode reader of the embodiment of the sample analyzer of FIG. 1.
Figure 6:
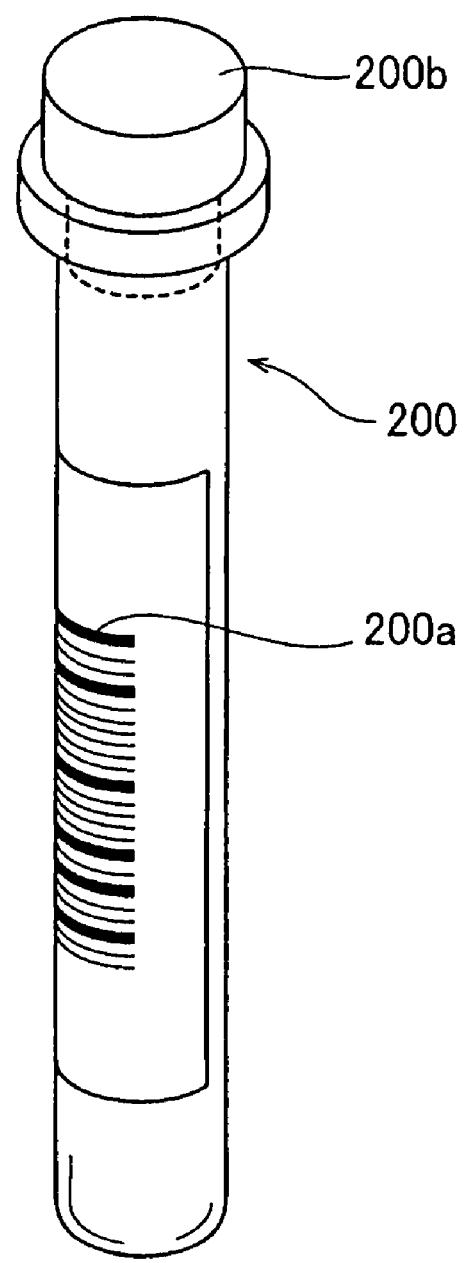
FIG. 6 is a perspective view of a blood collection tube containing sample.
Figure 7:
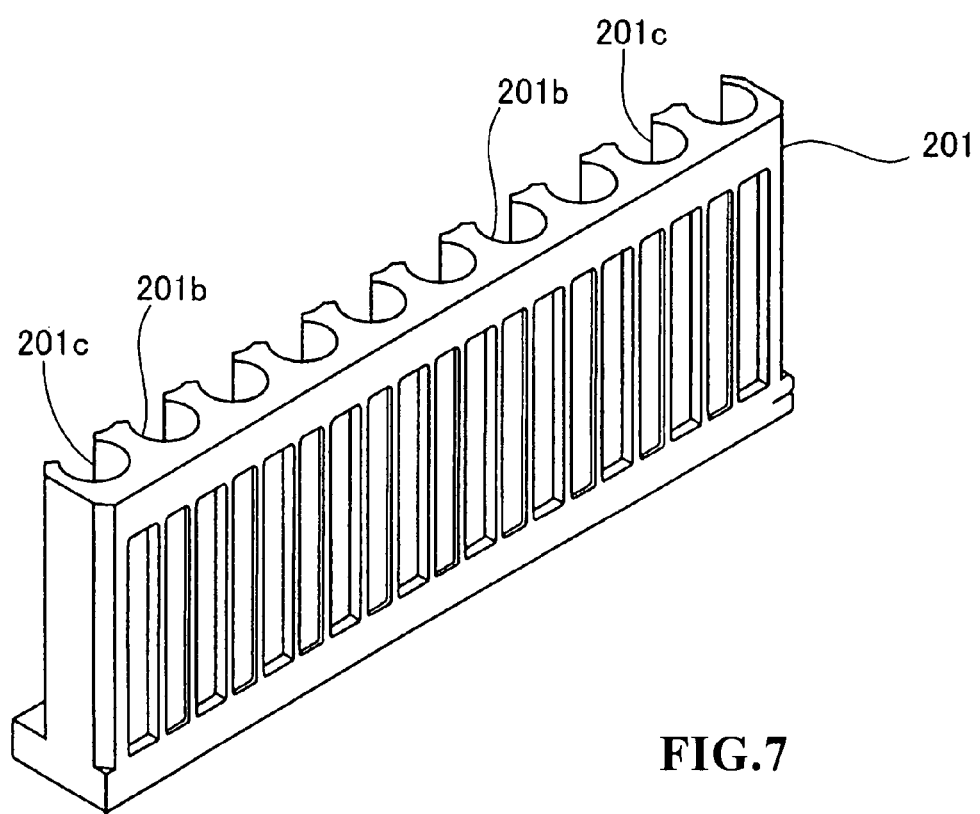
FIG. 7 is a perspective view of a rack used in the embodiment of the sample analyzer of FIG. 1.
Figure 8:
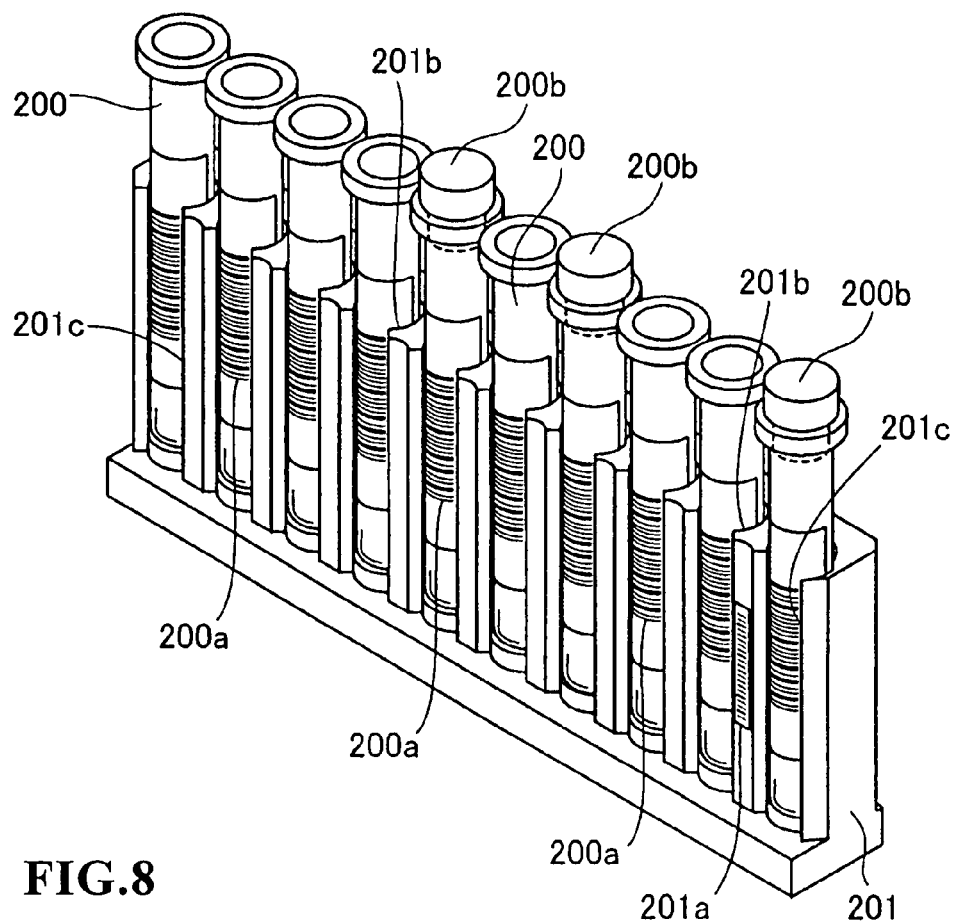
FIG. 8 is a perspective view showing blood collection tubes loaded in a rack.
Figure 9:
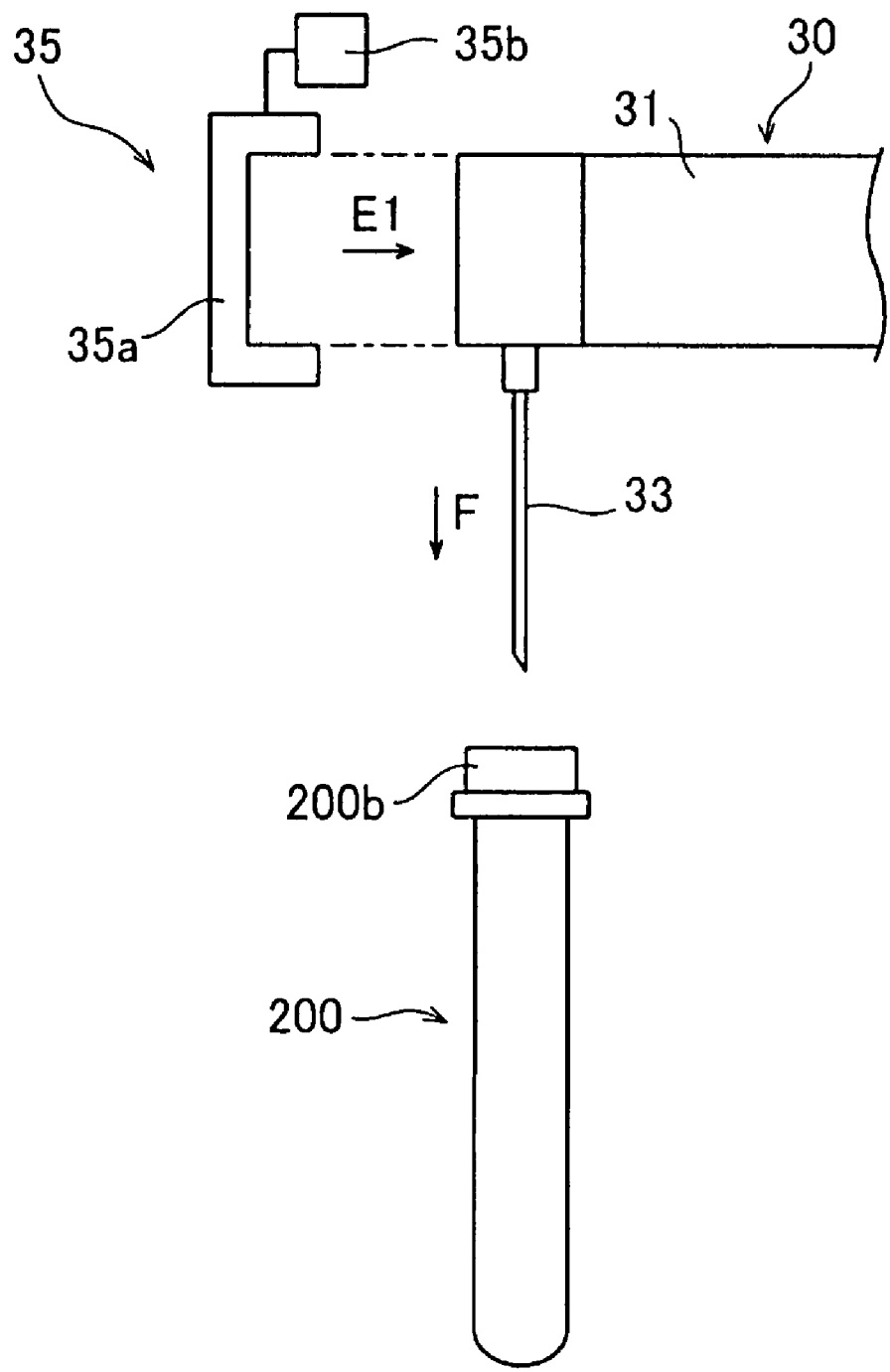
FIG. 9 is a schematic view of an auxiliary device of the embodiment of the sample analyzer of the present invention.
Figure 10:
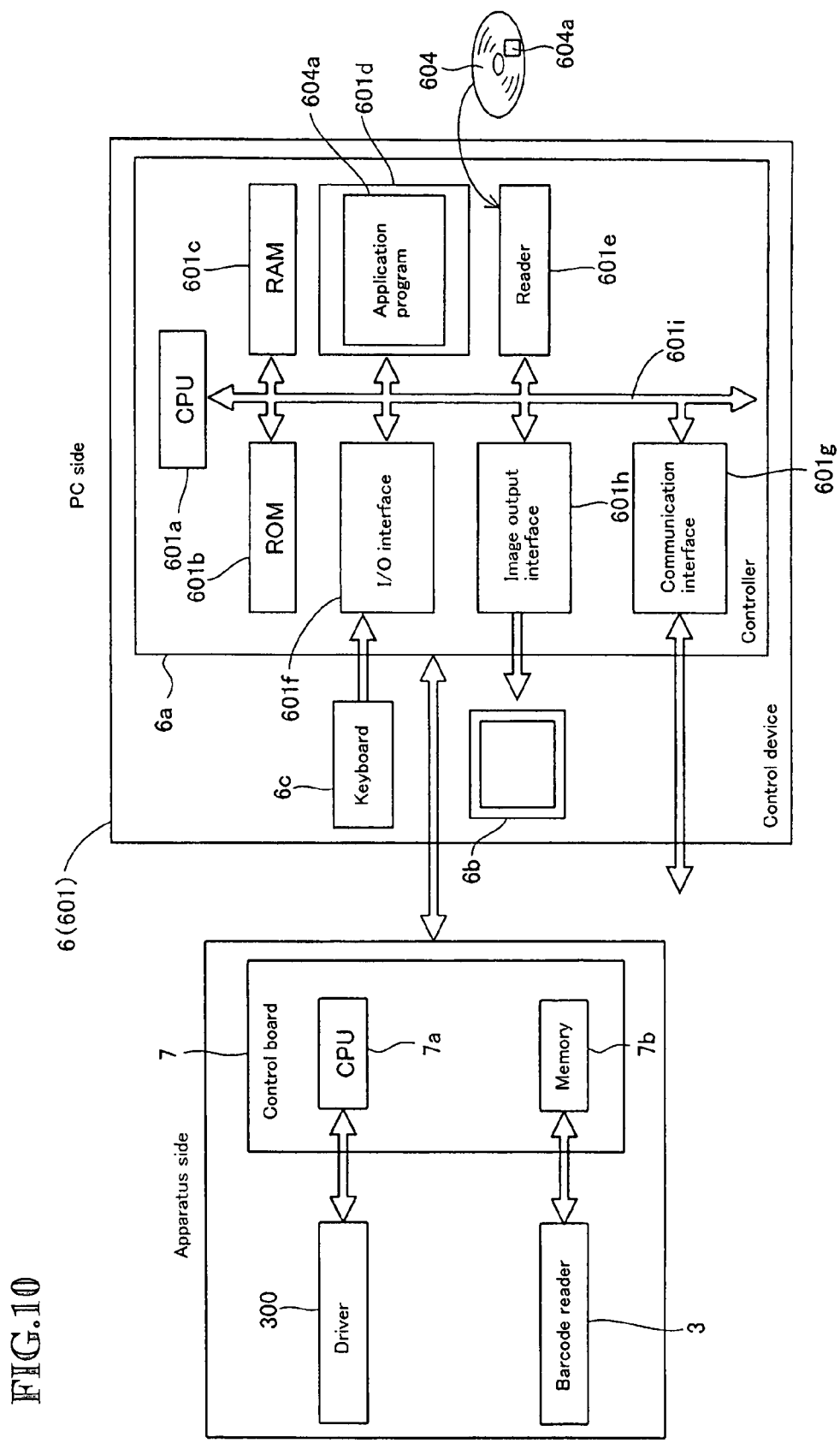
FIG. 10 is a block diagram of the control device and control board of an embodiment of the sample analyzer of the present invention.
Figure 11:
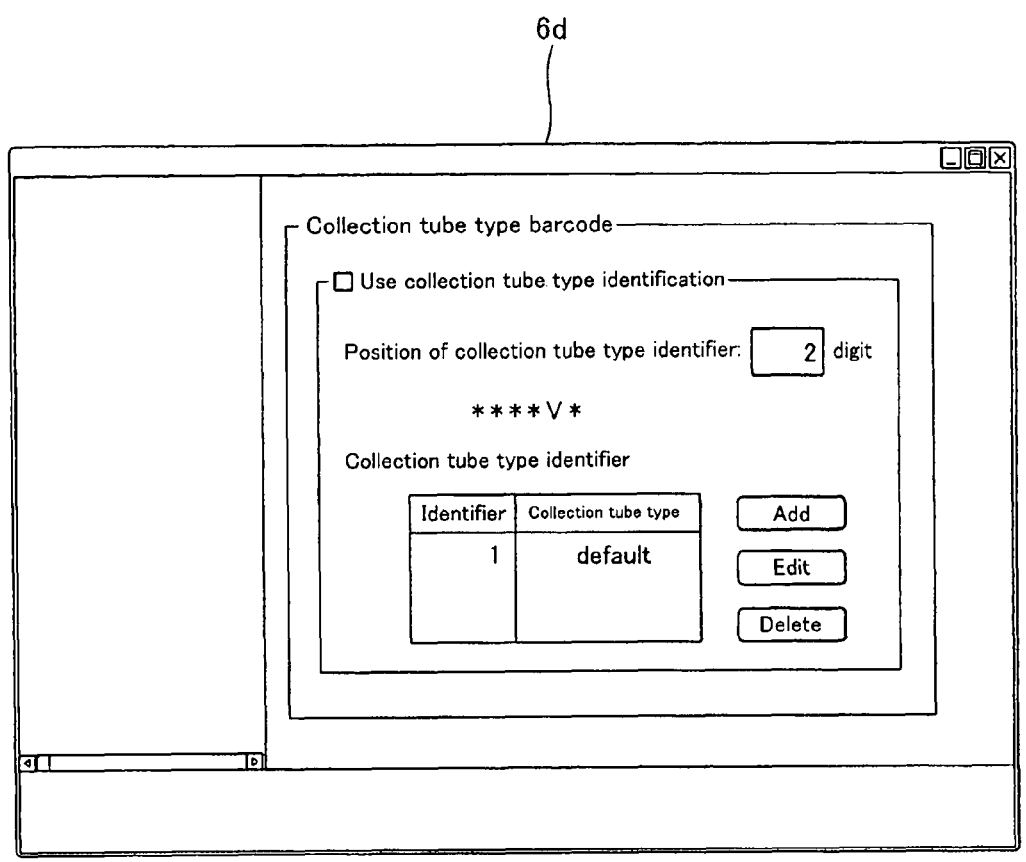
FIG. 11 illustrates the setting screen displayed on the display device of the control device.

FIGS. 1 through 3 show the general structure of an embodiment of the sample analyzer of the present invention. FIGS. 4 and 5 are enlarged perspective views that center on the transporting device of the embodiment of the sample analyzer of the present invention. FIGS. 6 through 8 show the blood collecting tubes and racks used in the embodiment of the sample analyzer of the present invention. FIGS. 9 through 11 illustrate details of the embodiment of the sample analyzer of the present invention. FIGS. 1 through 11 illustrate the structure of a sample analyzer 1, an embodiment of the present invention.

The embodiment of the sample analyzer 1 optically measures and analyzes the amount and activity of specific substances found in blood related to coagulation and fibrinolysis, and uses blood plasma as a sample. In the sample analyzer 1 of the present embodiment, coagulation time of a blood sample is measured by optically measuring the blood sample using the coagulation time method, synthetic substrate method, immunoturbidity method, and platelet aggregation method.

As shown in FIGS. 1 and 2, the sample analyzer 1 is configured by a transporting device 2, barcode reader 3 disposed near the transporting device 2, transmission type sensor 4, detecting device 5, and a control device 6 which is electrically connected to the detecting device 5. The transporting device 2, barcode reader 3, sensor 4, and detecting device 5 are controlled by a control board 7 provided within the detecting device 5 (refer to FIG. 3).

The transporting device 2 has the function of transporting a rack 201 loaded with a plurality (ten, in the present embodiment) of blood collection tubes 200 containing blood samples to the aspirating position P (refer to FIG. 3). Furthermore, the transport device 2 has a rack set region 2a that accommodates the racks 201 that hold the test tubes 200 containing unprocessed blood samples, a sample aspirating region 2b for performing the sample aspirating operation, and a rack receiving region 2c that accommodates the racks 201 that hold test tubes 200 containing processed blood samples. The rack set region 2a and rack receiving region 2c are respectively capable of accommodating five racks 201. As shown in FIGS. 4 and 5, the rack set region 2a is provided with slots 2e in which a pair of slidable hook members 2d slide in the arrow A direction to transport a rack 201 that has been placed in the rack set region 2a to the sample aspirating region 2b. When placed in the rack set region 2a, a rack 201 is pushed by the pair of hook members 2d and transported in the arrow A direction. The sample aspirating region 2b is provided with a pair of slots 2g which house a pair of rack members 2f, and a guide 2h for guiding the movement of the rack 201 in the sample aspirating region 2b. The pair of rack members 2f function to transport the rack 201 in the arrow B direction a single blood collection tube at a time by engaging a plurality of concavities (not shown in the drawing) provided on the bottom surface of the rack 201. The rack receiving region 2c is provided with an extruding member 2i which is slidable in the arrow C direction. When transported from the sample aspirating region 2b to the rack receiving region 2c, a rack 201 is pushed in the arrow C direction by the extruding member 2i. This configuration prevents jamming of a subsequent following rack 201.

In the present embodiment, the barcode reader 3 is provided to read the barcodes 200a and 201a that are respectively adhered to the blood collection tube 200 and rack 201. The barcode reader 3 is mounted so as to be slidable on a slide rail 5a provided on the side surface of the detecting device 5 on the transporting device 2 side. The barcode reader 3 reads the barcodes 200a and 201a respectively adhered to each blood collecting tube 200 and rack 201 as the rack slides along. This aspect will be described in detail later.

The blood collection tube 200 and the rack 201, which holds the blood collection tubes 200, are described below. The blood collection tube 200 contains a sample (blood) collected at a hospital or the like. As shown in FIG. 6, a barcode 200a is adhered to the blood collection tube 200. The barcode 200a includes information on the collected sample (blood), and information on the patient from whom the sample was collected. Blood collection tubes 200 come in various types which have different lengths, bottom heights, and diameters. In the present embodiment, the operation of a sample dispensing arm 30, which is described later, is controlled in conjunction with the type of blood collection tube 200. The blood collection tube 200 may be covered by a cap 200b. The present embodiment is configured so as to aspirate a sample by different aspirating operations depending on whether or not the collection tube 200 is provided with a cap 200b.

As shown in FIGS. 7 and 8, the rack 201 is provided with ten holders 201b. Each of the ten holders 201b respectively accommodates a single blood collection tube 200. When the blood collection tube 200 is smaller than the holder 201b, an adapter (not shown in the drawings) can be used to accommodate the blood collection tube 200 so that the tube is stable while held. The holders 201b of the rack 201 are provided with openings 201c for the barcode reader 3 to read the barcode of the blood collection tube 200, as shown in FIG. 8.

In the present embodiment, the barcode 201a (refer to FIG. 8), which identifies the type of blood collection tube 200 containing the sample, is adhered to the rack 201. A user loads the rack 201 so that only a one type of blood collection tube 200 corresponding to the value of the barcode 201a is loaded in a single rack 201. That is, the type of blood collection tube 2300 loaded in the rack 201 is identified when the barcode reader 3 reads the value of the barcode 201a. The correspondence between the value of the barcode 201a and the type of blood collection tube 200 can be set by the control device 6. This aspect will be described in detail later.

As shown in FIGS. 3 through 5, the transmission type sensor 4 is provided to determine whether or not a cap 200b is provided on the blood collection tube 200. The sensor 4 is provided above the sample aspirating region 2b. The sensor 4 includes a light emitting part (not shown in the drawings) and a light receiving part (not shown in the drawings) provided in opposition so as to interpose therebetween the open part and the cap 200b of the blood collection tube 200. When the blood collection tube 200 is provided with a cap 200b, the light receiving part does not receive the light emitted from the light emitting part because the light is blocked by the cap. When the blood collection tube 200 is not provided with a cap 200b, the light receiving part receives the light emitted from the light emitting part. Thus, the transmission type sensor 4 can determine whether or not a cap 200b is provided on the blood collection tube 200.

The detecting device 5 is capable of obtaining optical information of a supplied blood sample by optically measuring the blood sample supplied from the transporting device 2. In the present embodiment, optical measurement is performed on a blood sample dispensed into a cuvette 250 (refer to FIG. 4) of the detecting device 5 from a blood collection tube 200 loaded in a rack 201 of the transporting device 2. As shown in FIGS. 1 and 2, the detecting device 5 is provided with a cuvette supplier 10, rotating part 20, sample dispensing arm 30, lamp unit 40, reagent dispensing arm 50, cuvette moving part 60, measuring part 70 (refer to FIG. 3), urgent sample acceptor 80 (refer to FIG. 3), and fluid part 90.

The cuvette supplier 10 is capable of sequentially supplying a plurality of cuvettes 250 directly loaded by the user to the rotating part 20. As shown in FIGS. 1 through 3, the cuvette supplier 10 includes a first hopper 11a, second hopper 11b that is smaller than the first hopper 11a and is supplied cuvettes 250 from the first hopper 11a (refer to FIG. 3), two guide plates 12 for supplying cuvettes 250 from the second hopper 11b, support table 13 disposed below the bottom end of the two guide plates 12, and catchers 14 provided at predetermined spacing from the support table 13. The cuvettes 250 within the first hopper 11a move through the second hopper 11b, which is smaller than the first hopper 11a, and fall from the top of the two guide plates 12 toward the support table 13. The support table 13 functions to rotate the cuvettes 250 that have smoothly dropped along the guide plates 12 to a position at which the cuvette 250 can be grabbed by the catcher 14. The catcher 14 is provided to supply to the rotating part 20 those cuvettes 250 which have been moved by the support table 13.

As shown in FIG. 3, the detecting device 5 is provided with a disposal hole 15 for disposing of the cuvettes 250, and a waste box 16 disposed below the disposal hole 15 at a predetermined distance from the previously mentioned catcher 174. The catcher 14 disposes of the cuvette 250 on the cuvette transporting table 23 of the rotating part 20 through the disposal hole 15 and into the waste box 16. That is, the catcher 14 both supplies and disposes of the cuvettes 250.

The rotating part 20 is provided to transport in a rotational direction the cuvettes 250 supplied from the cuvette supplier 10, and reagent containers (not shown in the drawing) containing reagent for coagulating the blood sample. The rotating part 20 includes a circular reagent table 21, and annular reagent table 22 which is disposed on the outer side of the circular reagent table 21, and an annular cuvette transporting table 23 disposed on the outer side of the annular reagent table 22, as shown in FIG. 3. The cuvette transporting table 23, reagent table 21, and reagent table 22 are mutually and independently rotatable in both clockwise and counterclockwise directions.

The reagent tables 21 and 22 include a plurality of holes 21a and 22a provided at predetermined intervals along the circumferences of the respective reagent tables 21 and 22, as shown in FIG. 3. The holes 21a and 22a of the reagent tables 21 and 22 are provided for loading a plurality of reagent containers (not shown in the drawings) containing reagent for coagulating blood. The cuvette transporting table 23 includes a plurality of cylindrical holders 23a provided at predetermined intervals along the circumference of the cuvette moving table 23. The holder 23a is provided to hold the cuvettes 250 supplied from the cuvette supplier 10. A blood sample accommodated in a blood collection tube 200 held in a rack 201 loaded in the transporting device 2 is dispensed by the sample dispensing arm 30 into a cuvette 250 held in a holder 23a of the cuvette transporting table 23.

As shown in FIGS. 4 and 5, the sample dispensing arm 30 functions to aspirate a blood sample in a blood collection tube 200 that has been transported to the aspirating position P by the transporting device 2, and dispense the aspirated blood sample into a cuvette 250 that has been transported by the cuvette transporting table 23 (refer to FIG. 3). The sample dispensing arm 30 includes an arm 31, drive part 32 for driving the arm 31, pipette 33 mounted on the arm 31, and a fluid level sensor 34 that includes a fluid surface board 34a disposed on the top surface of the arm 31. The arm 31 is rotatable on a shaft 31a via a drive part 32, and is movable in vertical directions. The pipette 33 is made of metal and the tip of the pipette is cut at a sharply inclined angle. Thus, the pipette 33 can aspirate a blood sample even through a cap 200b when a cap 200b is provided on the blood collection tube 200. Moreover, the metal pipette 33 is connected to the fluid level detecting board 34a by wiring (not shown in the drawings). Thus, the fluid level can be detected based on the change in electrostatic capacitance when the tip of the pipette 33 contacts the fluid surface.

In the present embodiment, an auxiliary device 35 is provided near the sample dispensing arm 31, as shown in FIGS. 3 through 5. The auxiliary device 35 has an engaging member 35a which is slidable in the E direction, and a drive part 35b (refer to FIG. 9) which has a stronger drive force than the drive part 32. The engaging member 35a is movable in vertical direction via the drive force of the drive part 35b. When the transmission type sensor 4 has detected a cap 200b provided on the blood collection tube 200, the engaging member 35a engages the arm 31, and the arm 31 and pipette 33 descend via the drive force of the drive part 35b of the auxiliary device 35 which has a drive force that is stronger than the drive force of the drive part 32. The arm 31 and the pipette 33 descend through the cap 200b via the drive force of the drive part 35b of the auxiliary device 35.

The lamp unit 40 is provided to supply the light used by the measuring part 70 to perform optical measurements, as shown in FIG. 3.

The reagent dispensing arm 30 is provided to mix the reagent with the sample within the cuvette 250 by dispensing the reagent within a reagent container (not shown in the drawing) loaded in the rotating part 20 to a cuvette 250 which is held in the rotating part 20, as shown in FIGS. 1 through 3. A measurement sample is prepared by adding reagent to a blood sample. The cuvette moving part 60 is provided to move the cuvette 250 between the cuvette transporting table 23 of the rotating part 20, and the measuring part 70.

The measuring part 70 is provided to heat a measurement sample prepared by mixing reagent with a blood sample, receive light over time from the measurement sample which is irradiated with light of a plurality of wavelengths emitted from the lamp unit 40, and obtain optical information over time at the various light wavelengths. Specifically, the measuring part 70 obtains the amount of transmission light over time periods using light of several types emitted from the lamp unit 40.

The control board 7 is disposed below the measuring part 70. The control board 7 functions to control the operation of the detecting device 5, transporting device 2 and the like, and processes and stores optical information (electrical signals) output from the measuring part 70. The control board 7 includes a CPU 7a, memory 7b and the like. The CPU 7a controls the drivers 300 of the various devices provided in the apparatus body (detecting device 5, transporting device 2 and the like). The value of the barcode 201a of the rack 201, which is read by the barcode reader, is stored in the memory 7b.

As shown in FIG. 3, the urgent sample accepter 80 is provided to perform sample analysis processing for blood samples that require urgent handling. The urgent sample accepter 80 of interrupting an urgent sample when a blood sample supplied from the transporting device 2 is undergoing sample analysis processing. The fluid part 90 is provided to supply fluids such as washing fluids and the like to nozzles provided in each dispensing arm when the sample analyzer 1 performs a shutdown process, as shown in FIGS. 1 and 2.

The control device 6 (refer to FIG. 1) is a personal computer (PC), and includes a controller 6a configured by a CPU, ROM, RAM and the like, a display part 6b, and keyboard 6c. The display part 6b is provided to display analysis results (coagulation time) obtained by analyzing digital signal data transmitted from the measuring part 70.

In the present embodiment, the correspondence between the barcode 201a adhered to the rack 201, and the blood collection tube 200 held in the rack 201 can be set in the control device 6. Specifically, the correspondence between the type of blood collection tube, the value of the identifier and the position of the blood collection tube identifier in the barcode 201a adhered to the rack 201 can be set in a setting screen 6d displayed on the display part 6b, as shown in FIG. 11. The identifier value is settable to a maximum of ten types (0 through 9). In the example of FIG. 11, the type of blood collection tube held in the rack 201 is identified as the [default] type when the second digit value is [1] in a barcode of the rack 201 which has a six digit value.

The structure of the control device 6 is described below. As shown in FIG. 10, the control device 6 is configured by a computer 601 which mainly includes a controller 6a, display part 6b, and keyboard 6c. The controller 6a is mainly configured by a CPU 601a, ROM 601b, RAM 601c, hard disk 601d, reading device 601e, I/O interface 601f, communication interface 601g, and image output interface 601h. The CPU 601a, ROM 601b, RAM 601c, hard disk 601d, reading device 601e, I/O interface 601f, communication interface 601g, and image output interface 601h are connected by a bus 601i.

The CPU 601a is capable of executing computer programs stored in the ROM 601b, and computer programs loaded in the RAM 601c. The computer 601 functions as the control device 6 when the CPU 601a executes an application program 604a, which is described later.

The ROM 601b is configured by a mask ROM, PROM, EPROM, EEPROM or the like, and stores computer programs executed by the CPU 601a, as well as data and the like used in conjunction therewith.

The RAM 601c is configured by SRAM, DRAM or the like. The RAM 601c is used when reading the computer program recorded in the ROM 601b and on the hard drive 601d. The RAM 601c is further used as a work area of the CPU 601a when these computer programs are being executed.

The hard drive 601d contains various installed computer programs to be executed by the CPU 601a such as an operating system and application programs and the like, as well as data used in the execution of these computer programs. Also installed on the hard disk 601d is the application program 604a used in the blood coagulation time measurement in the present embodiment.

The reading device 601e is configured by a floppy disk drive, CD-ROM drive, DVD-ROM drive or the like, and is capable of reading the computer programs and data stored on a portable recording medium 604. Furthermore, the portable recording medium 604 may also store the application program 604a in the present embodiment; the computer 601 is capable of reading the application program 604a from the portable recording medium 604 and installing the application program 604a on the hard disk 601d.

Not only may the application program 604a be provided by the portable recording medium 604, the application program 604a also may be provided from a communication-capable external device connected to the computer 601 by an electric communication line (wire line or wireless) so as to be transmitted over the electric communication line. For example, the application program 604a may be stored on the hard disk of a server computer connected to the internet, such that the computer 601a can access the server computer and download the application program 604a, and then install the application program 604a on the hard disk 601d.

Also installed on the hard disk 601d is an operating system providing a graphical user interface, such as, for example, Windows (registered trademark) of Microsoft Corporation, U.S.A. In the following description, the application program 604a of the present embodiment operates on such an operating system.

The I/O interface 601f is configured by a serial interface such as a USB, IEEE1394, RS232C or the like, parallel interface such as SCSI, IDE, IEEE1284 or the like, analog interface such as a D/A converter, A/D converter or the like. The keyboard 6c is connected to the I/O interface 601f, such that a user can input data in the computer 601 using the keyboard 6c.

The communication interface 601g is, for example, and Ethernet (registered trademark) interface. The computer 601 can send and receive data to and from the detecting device 52 using a predetermined communication protocol via the communication interface 601g.

The image output interface 601h is connected to the display part 6b configured by an LCD, CRT or the like, such that image signals corresponding to the image data received from the CPU 601a can be output to the display 6b. The display part 6b displays an image (screen) in accordance with the input image signals.

The application program 604a used for blood coagulation time measurement, which is installed on the hard disk 601d of the controller 6a, measures the coagulation time of a blood sample using the amount of transmission light (digital signal data) of the measurement sample transmitted from the measuring part 70 of the detecting device 5. This coagulation time is the time from the addition of the reagent for coagulating the blood sample in the cuvette 250 until the measurement sample (the blood sample with added reagent) loses fluidity (coagulation time). The coagulation reaction during which the measurement sample loses fluidity is a reaction in which fibrinogen in the blood sample is changed to fibrin by the added reagent. In the sample analyzer 1 of the present embodiment, the coagulation reaction, which is dependent on the amount of fibrinogen in the blood sample, is confirmed by the amount of change in the transmission light of the measurement sample (the difference between the amount of transmission light before the reaction and the amount of transmission light after the reaction).

Figure 12:
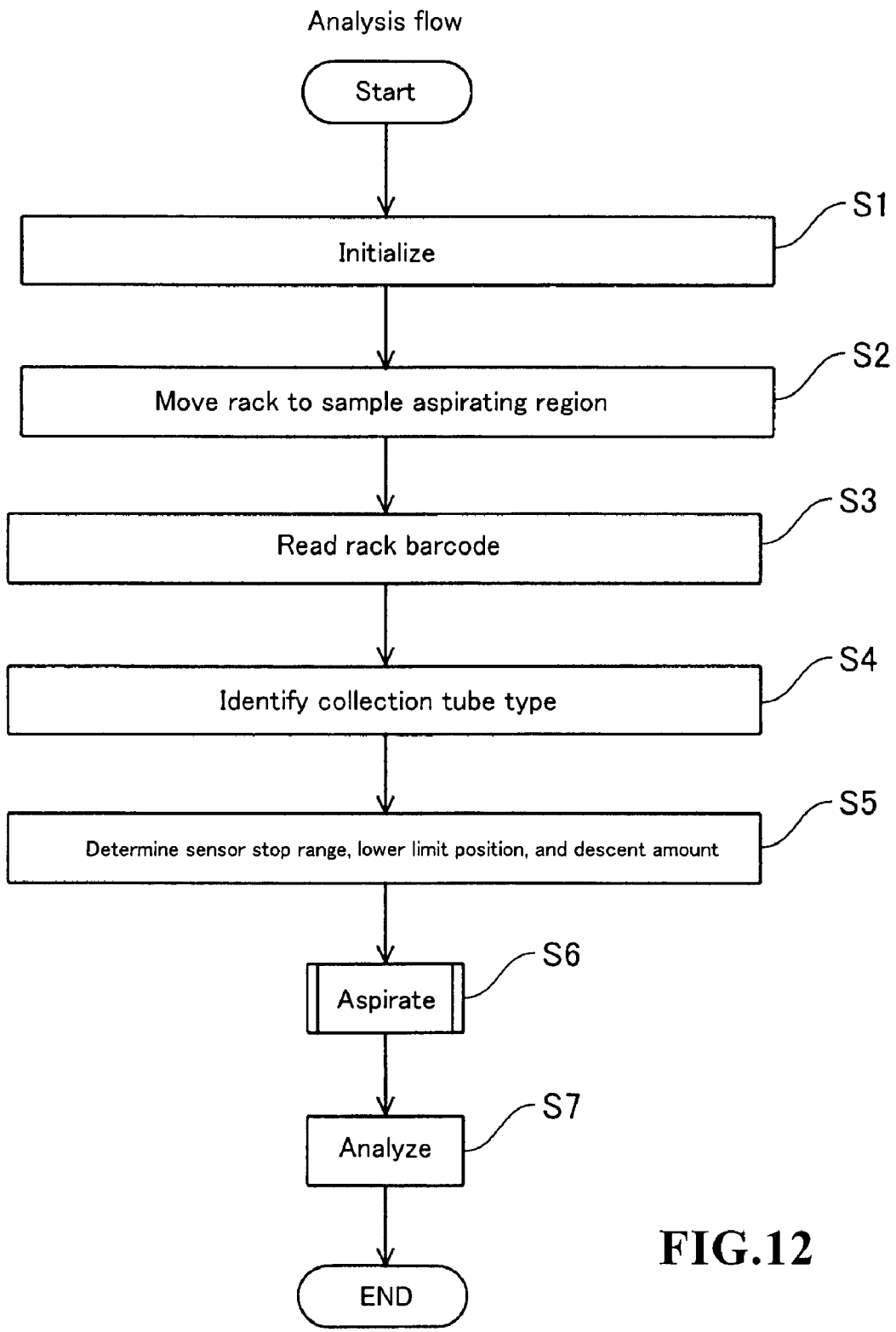
FIG. 12 is a flow chart illustrating the analyzing operation of the embodiment of the sample analyzer of the present invention.

FIG. 12 is a flow chart illustrating the analyzing operation of the present embodiment of the sample analyzer 1. The analyzing operation of the sample analyzer 1 of the present embodiment is described below with reference to FIGS. 1, 4, and 12.

The sample analyzer 1 is first initialized in step S1 by turning ON the power sources of the control device 6 and the apparatus body of the analyzer 1 (detecting device 5 and the like) shown in FIG. 1. Thus, the software stored in the controller 6a of the control device 6 is initialized, and an operation is performed to return each dispensing arm and the devices for moving the cuvettes 250 to their initial positions.

In the transporting device 3 shown in FIG. 4, the rack 201 placed in the rack set region 2a is moved in the arrow A direction to the sample aspirating region 2b by sliding on the pair of hook members 2d in step S2. Then, in step S2 of FIG. 12, the barcode 200a of the blood collection tubes 200, and the barcode 201a of the rack 201 are read by the barcode reader in the sample aspirating region 2b. The reading of the barcode is described in detail below.

The rack 201 that has been moved to the sample aspirating region 2b is first transported one blood collection tube at a time in the arrow B direction by the hook member 2f. In parallel with the transporting of the rack 201 in the arrow B direction, the barcode reader 3 reads the barcode 200a of the blood collection tube 200 held in the rack 201 as well as the barcode 201a of the rack 201 as the rack 201 slides in the D direction. The rack identifying information that identifies the rack is obtained by reading the barcode 201a of the rack 201. The rack identifying information includes a container type identifier that identifies the type of the blood collection tube 200 held in the rack 201. Information concerning the sample (blood) contained in the blood collection tube 200 is obtained by reading the barcode 200a of the blood collection tube 200. The barcode 200a of the blood collection tube 200 is read twice. That is, the barcode reader 3 reads the barcode 200a of the blood collection tube 200 and the barcode 201a of the rack 201 as they slide along until the final blood collection tube 200 containing sample to be aspirated has moved to the aspirating position P. Prior to aspiration, the barcode reader 3 rereads the barcode of the blood collection tube 200 that contains the sample to be aspirated. The second reading verifies the sample to be aspirated.

In step S4, the type of blood collection tube 200 is identified. Specifically, the control board 7 refers to the correspondence between the type of blood collection tube and the container type identifier set in the control device 6, and identifies the type of blood collection tube 200 that corresponds to the container type identifier of the barcode 201a read from the rack 201. The correspondence between the blood collection tube type and the container type identifier is set on the setting screen 6d shown in FIG. 11.

In step S5, the stop range during which the fluid level detection function of the sensor 4 is stopped, the lower limit position corresponding to the lower limit value of the minimum amount of sample necessary for measurement, and the amount of descent of the pipette 33 from the fluid level are determined. These values are determined in accordance with the type of blood collection tube 200 identified in step S4. The control board 7 obtains these values (stop range, lower limit position, and amount of descent) from the controller 6a of the control device 6.

In step S6, the control board 7 aspirates the sample via the auxiliary device 35 and sample dispensing arm 30 based on the obtained stop range, lower limit position, and amount of descent. The sample aspirating operation will be described in detail later.

In step S7, the aspirated sample is analyzed. The sample analysis operation is described in detail below. In step S6, the sample which has been aspirated by the sample dispensing arm 30 is first dispensed to a cuvette 250 on the cuvette transporting table 23 of the rotating part 20, as shown in FIG. 3. The cuvette 250 that contains the sample is transported near the measuring part 70 by rotating the cuvette transporting table 23. Then, the cuvette 250 is moved to the measuring part 70 by the cuvette moving part 60. Reagent from the reagent container (not shown in the drawing) on the reagent table of the rotating part 20 is dispensed by the reagent dispensing arm 50 to the cuvette 250 that contains the sample. Thus, a measurement sample is prepared by mixing reagent and sample. The measurement sample is optically measured in the measuring part 70 by irradiating the measurement sample with light from the lamp unit 40, and the measurement result is obtained by the CPU 7a of the control board 7. Thereafter, the measurement result is sent from the control board 7 to the control device 6, and the control device 6 analyzes the measurement result finally, the control device 6 displays the analysis result is on the display part 6b, which ends the analysis performed by the sample analyzer of the present embodiment.

Figure 13:
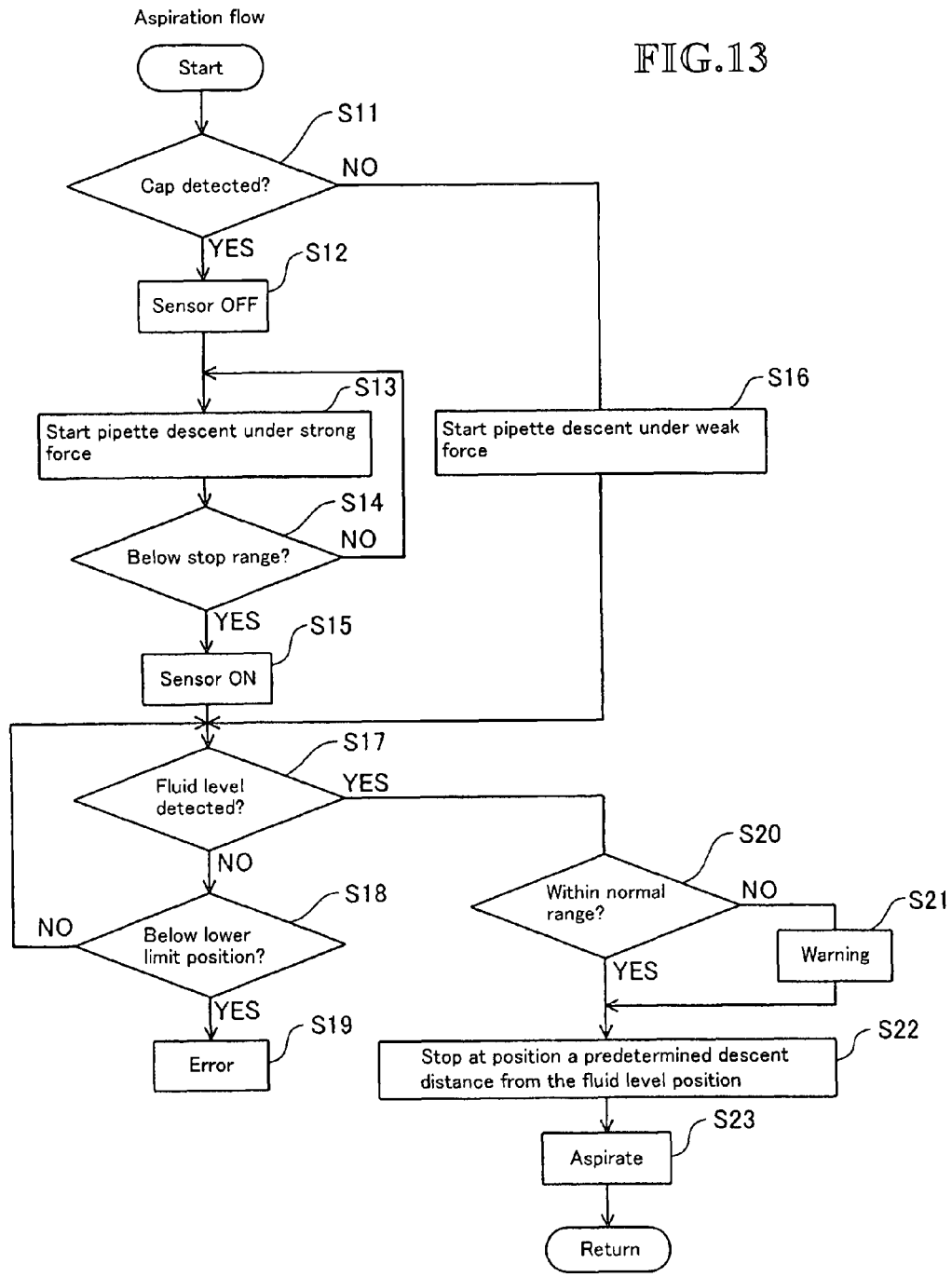
FIG. 13 is a flow chart illustrating the aspirating operation of the embodiment of the sample analyzer of the present invention.
Figure 14:
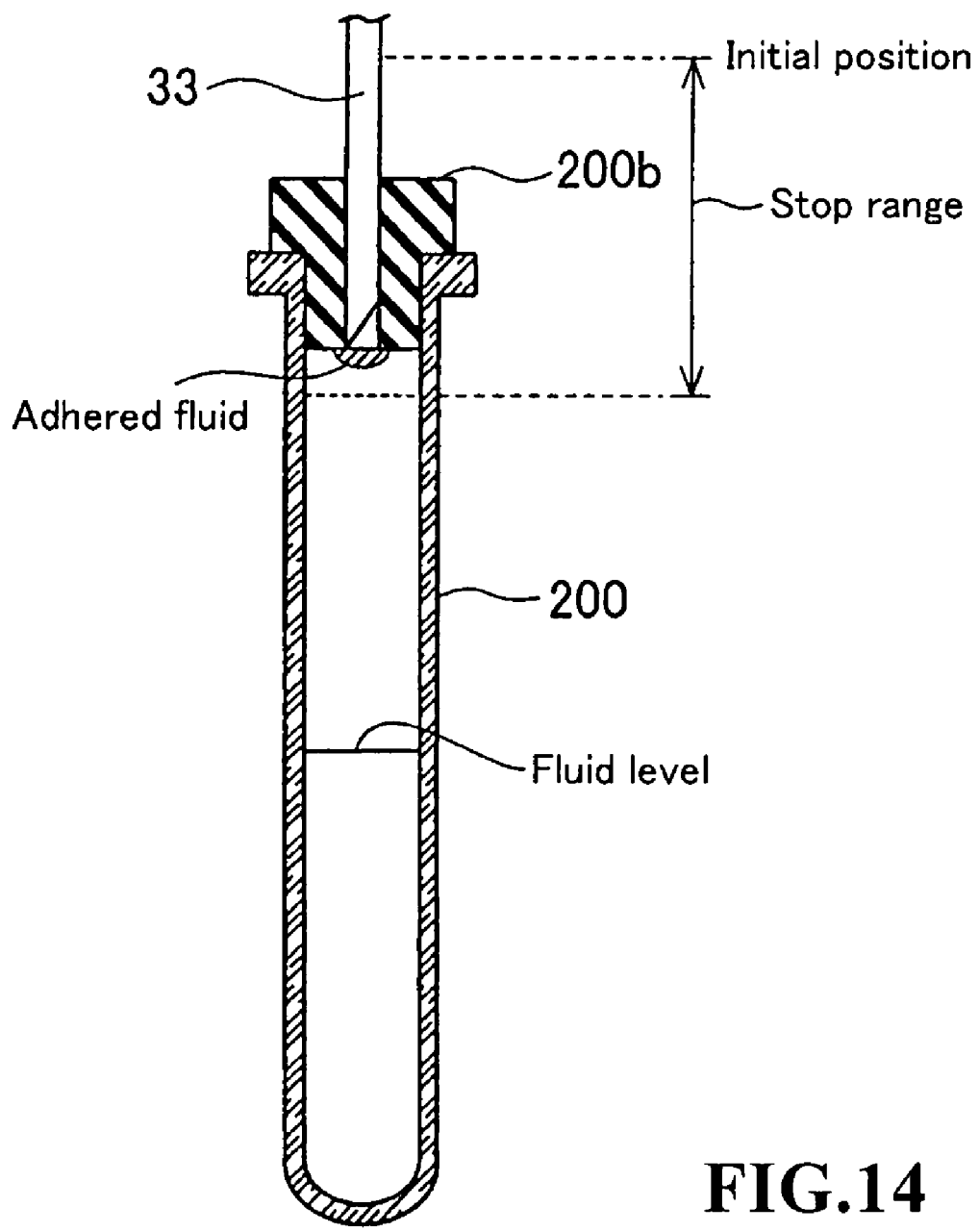
FIG. 14 is a cross section view of a blood collecting tube illustrating the stopping range in which the fluid level sensor is stopped.
Figure 15:
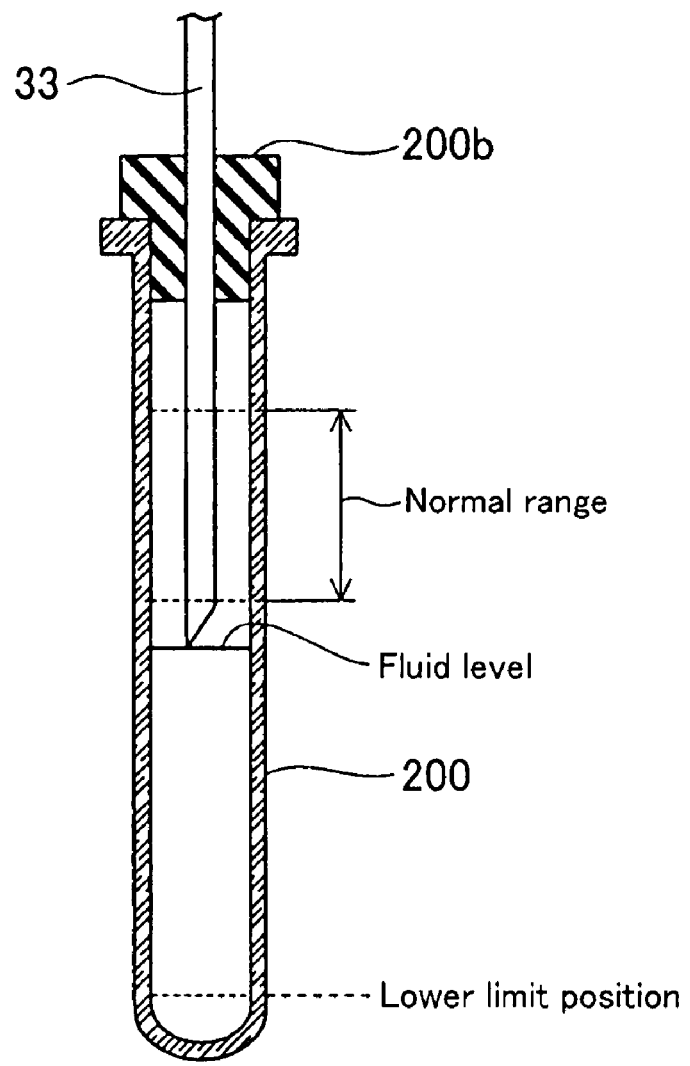
FIG. 15 is a cross section view of a blood collection tube illustrating the normal range and lower limit position of a sample.
Figure 16:
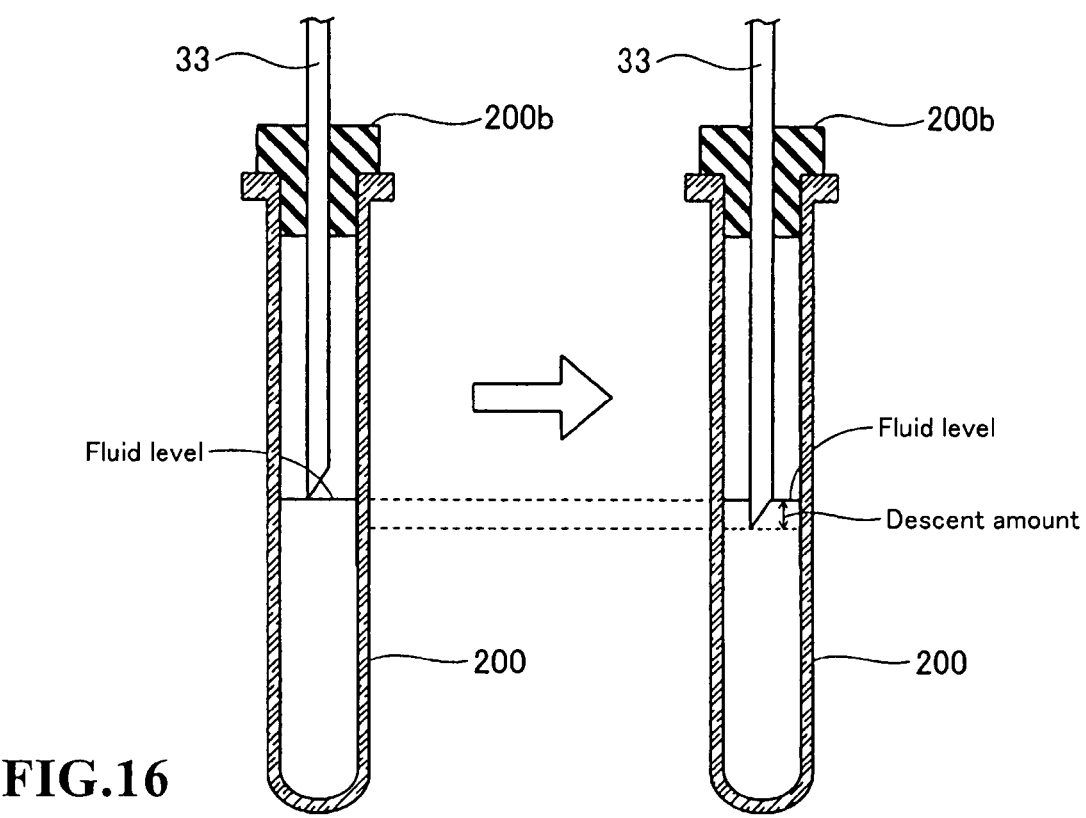
FIG. 16 is a cross section view of a blood collecting tube illustrating the amount by which the pipette descends.

FIG. 13 is a flow chart illustrating the sample aspirating operation by the sample dispensing arm of the sample analyzer of the present embodiment. FIGS. 14 through 16 illustrate details of the control of the aspirating operation performed by the control board 7. The sample aspirating operation performed by the sample dispensing arm 30 of the present embodiment of the sample analyzer 1 is described below with reference to FIGS. 2, 4, 9, and FIGS. 13 through 16.

As shown in FIG. 4, the blood collection tubes 200 that contain the samples are transported one tube at a time in the arrow B direction by the hook member 2f in the sample aspirating region 2b of the transporting device 2. As shown in step S11 of FIG. 13, a determination is made at this time as to whether or not the transmission type sensor 4 provided above the sample aspirating region 2b has detected a cap 200b on the blood collection tube 200. Then, the blood collection tube 200 is moved to the aspirating position P after the presence or absence of the cap 200b has been determined by the sensor 4. The sample dispensing arm 30 rotates to a position at which the pipette 33 is above the aspirating position P. When the sensor 4 has not detected a cap 200b, the routine continues to step S16, and the pipette 33 starts to descend with a weak force. Specifically, the arm 31 and pipette 33 of the sample dispensing arm 30 disposed above the aspirating position P are moved downward (arrow F direction in FIG. 2) by the drive part 32 of the sample dispensing arm 30. When the pipette 33 starts to descend, the routine moves to step S17. When, however, the sensor 4 has detected the presence of a cap 200b, the fluid level sensor 34 is turned OFF in step S12.

In step S13, the pipette 33 of the sample dispensing arm 30 starts to descend with a weak force. Specifically, the engaging member 35a of the auxiliary device 35 slides in the E1 direction in FIG. 9, and engages the arm 31 of the sample dispensing arm 30 positioned over the aspirating position P, as shown in FIGS. 2 and 9. Then, the arm 31 with the pipette 33 mounted thereon descends integratedly with the engaging member 35a in the arrow F direction by the drive part 35b (refer to FIG. 9) of the auxiliary device 35 that has a stronger drive force than the drive part 32 of the sample dispensing arm 30. At this time the drive part 32 of the sample dispensing arm 30 does not operate, and the arm 31 and pipette 33 descend only via the force of the drive part 35b of the auxiliary device 35. The cap 200b of the blood collection tube 200 is pierced by the sharply cut tip of the pipette 33 via the descent of the pipette 33 under a strong force, and the sample within the blood collection tube 200 can be aspirated.

In step S14, a determination is made as to whether or not the tip of the pipette 33 is below the stop region of the fluid level sensor 34 determined in accordance with the type of blood collection tube 200. The stop range of the fluid level sensor 34 is the range from the initial position from which the pipette 33 starts to descend to a position a predetermined distance below the bottom surface of the cap 200b. When the tip of the pipette 33 is within the stop range, steps S13 and S14 are repeated. However, when the tip of the pipette 33 is below the stop range, the fluid level sensor is turned on in step S15, and the routine moves to step S17.

In step 17, a determination is made as to whether or not the fluid level sensor 34 has detected the fluid level of the sample. Specifically, whether or not there has been a change in the electrostatic capacitance is detected by fluid level detecting board 34a connected by wire (not shown in the drawing) to the pipette 33 when the tip of the metal pipette 33 in the air contacts the surface of the fluid. When the fluid level is detected, the routine moves to step S20. However, when the fluid level is not detected, the tip of the pipette 33 descends below the lower limit position (refer to FIG. 15) determined in accordance with the type of blood collection tube 200 in step S18. This lower limit corresponds to the amount of sample that ensures an aspiration amount necessary to measure the sample. That is, since the blood collection tube 200 does not contain the amount of sample required for measurement when the tip of the pipette 33 is positioned below the lower limit and the fluid level has not been detected, and error is generated in step S19, an error display is shown on the display part 6b of the control device 6 and a warning sound is generated. In this case, the aspirating operation is terminated for the blood collection tube 200 that has generated the error, and an aspirating operation is started for the next blood collection tube 200. However, when the tip of the pipette 33 is positioned above the lower limit, steps S17 and S18 are repeated until an error occurs in the fluid level detection.

When the fluid level is detected in step S17, a determination is made in step S20 as to whether or not the position of the detected fluid level is within the normal range (refer to FIG. 15). The normal range is the quantity range of normally collected sample during blood collection. When a collected sample quantity is not in the normal range in the blood collection tube 200, accurate measurement can not be performed because the ratio of anticoagulant added beforehand to the blood collection tube 200 to prevent coagulation is not normal relative to the amount of blood. When the position of the detected fluid level is in the normal range, the routine moves to step S22. However, the user is alerted when the fluid level is not in the normal range, because it is difficult to obtain an accurate measurement result. After the warning, the routine moves to step S22.

In step S22, the pipette 33 is stopped at a position (descent position) descended a predetermined amount from the fluid level position detected in step S17. The descent amount (refer to FIG. 16) is determined in accordance with the type of blood collection tube 200, and corresponds to the amount of sample to be aspirated in a single aspiration. In step S23, sample is aspirated by the pipette 33. The amount of sample adhering to the outer surface of the pipette 33 can be minimized by aspirating sample when the pipette 33 is descended only the descent amount from the fluid level position. This is the manner in which sample is aspirated in the present embodiment.

In the present embodiment described above, a blood collection tube type identifier of a blood collection tube 200 held in a rack 201 can be obtained by reading the barcode 201a of the rack 201 via a barcode reader 3 that reads the blood collection tube type identifier from the barcode 201a of the rack 201. An operation to re-adhering the barcode 200a of the blood collection tube 200 is unnecessary because the type of blood collection tube 200 can be identified by the blood collection tube type identifier obtained from the barcode 201a of the rack 201. Thus, reduced testing efficiency is prevented. Moreover, there is no need to identify the shape (height and the like) of the blood collection tube 200 itself via sensors or complex controls since the shape of the blood collection tube 200 is identified when the barcode reader 3 simply reads the blood collection tube type identifier from the barcode 201a of the rack 201. Therefore, the apparatus is simplified.

In the present embodiment described above, the pipette 33 is lowered a minimum required descent amount from the fluid level to aspirate a sample by determining the descent distance the pipette 33 is to descend from the fluid surface then lowering the pipette 33 below the fluid level by this determined descent amount based on the blood collection tube type identifier read from the barcode 201a of the rack 201.

In the present embodiment described above, measuring an insufficient amount of sample can be prevented when there is an insufficient amount of sample needed for measurement available in the blood collection tube 200 because the aspiration operation is suspended and designated an error when the lower limit position of the fluid level of a sample needed for aspiration is determined and the pipette tip descends below the lower limit without the fluid level sensor 34 detecting the fluid level position based on the blood collection tube type identifier read from the barcode 201a of the rack 201.

In the present embodiment described above, whether or not a blood collection tube 200 contains a normal amount of sample to be aspirated can be easily determined by determining whether or not the amount of sample in a blood collection tube 200 is adequate based on the comparison result obtained by determining a predetermined normal amount range for samples based on the blood collection tube type identifier read from the barcode 201a of the rack 201, and comparing the predetermined normal amount and the fluid level position detected by the sensor.

In the present embodiment described above, when the fluid level position of a sample is outside the normal amount range, the user is able to recognize that the sample in the blood collection tube 20 is not a normal amount by the issued warning.

In the present embodiment described above, the stop range for stopping the detection function of the fluid level sensor 34 is determined based on the blood collection tube type identifier read from the barcode 201a of the rack 201 when the blood collection tube 200 is provided with a cap 200b to prevent the fluid level sensor 34 from erroneously detected fluid (sample and the like) adhering to the cap 200b as the fluid level position when fluid (sample and the like) adhere to the cap 200b by stopping the detection function of the fluid level sensor 34 until the fluid level sensor 34 is below the stop range.

The embodiments in this disclosure are not limited to the examples in any aspects. The scope of the present invention is expressed in the scope of the claims and not in the description of the embodiments, and includes all modifications within the scope of the claims and all meanings and equivalences appertaining thereto.

For example, although the above embodiment uses an example of determining the presence or absence of a cap 200b of a blood collection tube 200 by a transmission type sensor 34, the present invention is not limited to this method inasmuch as a value for determining the presence or absence of a cap on a blood collection tube loaded in a rack may be included in the barcode of the rack. Thus, the presence or absence of a cap on a blood collection tube can be determined by a value in a barcode read by a barcode reader without providing a sensor to detect the cap.

Although the above embodiment uses an example of a slidable barcode reader that reads the barcodes of blood collection tubes and rack while sliding, the present invention is not limited to this method inasmuch as the barcode reader may be stationary.

Although the above embodiment is described by way of an example in which a transporting device 2 is provided to transport a rack 201 containing blood collection tube 200 to the sample analyzer 1, the present invention is not limited to this arrangement inasmuch as a transporting device may be provided separately from the sample analyzer.

Although the above embodiment is described by way of an example providing a barcode reader 3 in the sample analyzer 1 to read the barcode 201a and barcode 200a of the rack 201 and the blood collection tubes 200, the present invention is not limited to this arrangement inasmuch as the barcode of the rack may be read by a barcode reader provided outside the sample analyzer, and the values of the read barcode may be received by a receiver. Such a configuration can also identify the type of blood collection tubes loaded in a rack.

Although the above embodiment is described by way of an example in which a barcode 201a is read by a barcode reader 3 and this barcode 201a records rack identifying information that identifies a rack 201 in order to identify the type of blood collection tubes loaded in the rack 201, this barcode 201a is adhered to the rack 201, and this barcode 201a includes in the rack identifying information a blood collection tube type identifier to identify the type of blood collection tubes, the present invention is not limited to this arrangement inasmuch as rack identifying information may be magnetically recorded on the rack 201 and read by a magnetic reading device. Even when a blood collection tube type identifier is not included in the rack identifying information, a table which represents the correspondence between a rack identified in rack identifying information and the type of blood collection tube loaded in that rack may be stored on the apparatus side, such that the type of corresponding blood collection tube can be determined from the rack identifying information by referencing this table.

Although the above embodiment has been described by way of an example in which one type of blood collection tube containing sample is loaded in a single rack, the present invention is not limited to this arrangement inasmuch as a plurality of types of blood collection tubes may be loaded in a single rack insofar as the blood collection tubes have mutually similar shapes.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A sample analyzer comprising:
   a transporting device configured to transport a rack for holding a plurality of containers containing samples respectively, the rack comprising a recording part in which identifying information is recorded, the identifying information comprising a container type identifier that identifies a type of container held by the rack;
   a reading device configured to read the identifying information from the recording part of the rack transported by the transporting device;
   an aspirating device comprising an aspirating tube and a moving device configured to move the aspirating tube in a direction to insert the aspirating tube in a container;
   a controller configured to determine, based on the identifying information read by the reading device, an insertion position for inserting the aspirating tube to aspirate a sample in a container and to control the moving device to execute an insert movement by inserting the aspirating tube in the container at the determined insertion position; and
   an analyzing part configured to analyze the sample aspirated by the aspirating device,
   wherein the controller is configured to control the moving device such that the moving device executes the insert movement for each of the plurality of containers held by the rack based on the identifying information read by the reading device.

2. The sample analyzer according to claim 1, further comprising
   a detecting device configured to detect a fluid level position in the container, wherein
      the moving device is further configured to move the aspirating tube in vertical directions; and
      the controller is further configured to determine, based on the identifying information ready by the reading device, descent amount value, and to control the moving device so that the aspirating tube descends into the container below the fluid level by the determined descent amount value.

3. The sample analyzer according to claim 2, wherein
   the controller is further configured to determine, based on the identifying information read by the reading device, a lower limit position value and to control the aspirating device so as to suspend the aspirating operation when the aspirating tube has moved below the lower limit position value without detecting fluid level by the detecting device.

4. The sample analyzer according to claim 1, further comprising a detecting device configured to detect a fluid level position in the container, wherein the controller is further configured to:

determine, based on the identifying information read by the reading device, whether or not the container is a closed container; and based on a determination that the container is a closed container:
- determine a stop range for stopping detecting the fluid level based on the identifying information read by the reading device; and
- cause the detecting device to stop detecting the fluid level until the aspirating tube descends through the stop range.

5. The sample analyzer according to claim 1, wherein the controller is further configured to determine, based on the identifying information read by the reading device, whether or not the container is a closed container, and to control operation of the aspirating device based on the determination result.

6. The sample analyzer according to claim 1, wherein the sample is a blood sample.

7. A sample analyzer comprising:
- a transporting device for transporting a rack for holding a plurality of containers containing samples respectively, the rack comprising a recording part in which a container type identifier identifying a type of containers held by the rack is recorded;
- a reading device for reading the container type identifier from the recording part of the rack transported by the transporting device;
- an aspirating device comprising an aspirating tube and a moving device configured to move the aspirating tube in a direction to insert the aspirating tube in a container;
- a controller for:
  - determining, based on the container type identifier, an insertion position for inserting the aspirating tube to aspirate a sample in a container;
  - controlling the moving device to execute an insert movement by inserting the aspirating tube in the container at the determined insertion position; and
- an analyzing part for analyzing the sample aspirated by the aspirating device,
wherein the controller controls the moving device such that the moving device executes the insert movement for each of the plurality of containers held by the rack based on the container type identifier read by the reading device.

* * * * *